US011173200B2

(12) United States Patent
Shackelton et al.

(10) Patent No.: US 11,173,200 B2
(45) Date of Patent: Nov. 16, 2021

(54) PHENOTYPICALLY WILD-TYPE AND GENETICALLY ATTENUATED VIRUSES

(71) Applicants: Laura Shackelton, Sammamish, WA (US); Matthew Kerner, Sammamish, WA (US)

(72) Inventors: Laura Shackelton, Sammamish, WA (US); Matthew Kerner, Sammamish, WA (US)

( * ) Notice: Subject to any disclaimer, the term of this patent is extended or adjusted under 35 U.S.C. 154(b) by 0 days.

(21) Appl. No.: 16/616,399

(22) PCT Filed: Jun. 1, 2018

(86) PCT No.: PCT/US2018/035587
§ 371 (c)(1),
(2) Date: Nov. 22, 2019

(87) PCT Pub. No.: WO2018/222983
PCT Pub. Date: Dec. 6, 2018

(65) Prior Publication Data
US 2020/0138936 A1  May 7, 2020

Related U.S. Application Data

(60) Provisional application No. 62/514,091, filed on Jun. 2, 2017.

(51) Int. Cl.
| | |
|---|---|
| *A61K 38/00* | (2006.01) |
| *C07K 14/47* | (2006.01) |
| *C12N 9/00* | (2006.01) |
| *C07K 14/00* | (2006.01) |
| *C07K 14/50* | (2006.01) |
| *A61K 39/12* | (2006.01) |
| *C12N 7/00* | (2006.01) |
| *C12N 15/81* | (2006.01) |
| *A61K 39/00* | (2006.01) |

(52) U.S. Cl.
CPC ............... *A61K 39/12* (2013.01); *C12N 7/00* (2013.01); *C12N 15/815* (2013.01); *A61K 2039/5254* (2013.01)

(58) Field of Classification Search
CPC .......... A61P 43/00; A61P 29/00; A61P 35/00; A61P 37/02; A61K 38/00
See application file for complete search history.

(56) References Cited

U.S. PATENT DOCUMENTS

| 4,687,737 | A | 8/1987 | Sharp et al. |
| 9,121,024 | B2 | 9/2015 | Tian et al. |
| 2013/0323821 | A1 | 12/2013 | Tian et al. |
| 2016/0317647 | A1 | 11/2016 | Giuseppe et al. |

FOREIGN PATENT DOCUMENTS

WO   WO 2010/037062 A1   4/2010

OTHER PUBLICATIONS

Wang et al., "Construction of a live-attenuated HIV-1 vaccine through genetic code expansion", Angew Chem Int Ed Engl. ,2014, 53(19): 4867-4871.*
Wang et al., "Construction of a Live-Attenuated HIV-1 Vaccine through Genetic Code Expansion", Angew Chem Int Ed Engl., 2014(19):4867-4871.*
National Center for Biotechnology Information "NCBI", "Genetic Codes", 2017 (online): pdf p. 1.*
Mühlhausen et al. (publicly available May 2016) "A novel nuclear genetic code alteration in yeasts and the evolution of codon reassignment in eukaryotes" *Genome Res.* May 2016, 26(7): 945-955.
ISR and Written Opinion dated Aug. 29, 2018 in PCT/US2018/035587, 33 pages.
Ohama et al. (1993) "Non-Universal Decoding of the Leucine Codon CUG in Several *Candida* Species." *Nucleic Acids Research* 21(17): 4039-4045.
Stanton (Apr. 2017) "CHO stopper? Biogen looks to alternative cell lines for future of bioproduction" *BioPharma Reporter,* available online at https://www.biopharma-reporter.com/Article/2017/04/28/Biogen-working-on-a-radical-departure-from-the-CHO-platform, 2 pages.
Timmer (Dec. 2016) "Virus engineered to rely on artificial amino acids, used as vaccine" *ARS Technica,* available online at https://arstechnica.com/science/2016/12/virus-engineered-to-rely-on-artificial-amino-acids-used-as-vaccine/, 5 pages.
Wang et al. (2014) "Construction of a live-attenuated HIV-1 vaccine through genetic code expansion" Angew Chem Int Ed Engl. 53(19): 4867-4871.
U.S. Appl. No. 16/616,402, filed Nov. 22, 2019.

* cited by examiner

*Primary Examiner* — Barry A Chestnut
(74) *Attorney, Agent, or Firm* — Leydig, Voit & Mayer, Ltd.

(57) ABSTRACT

The disclosed compositions and methods provide an approach for the rational development of a live attenuated virus to be used as a vaccine, vaccine seed strain, therapy, and/or research tool. Methods are disclosed to generate a virus that is phenotypically wild-type but genetically attenuated. The virus would 'look' like the pathogenic virus and, upon vaccination, the initial viral infection would be largely, if not fully, indistinguishable from that initiated by its pathogenic counterpart, leading to the most relevant and robust immune response. However, because the genome is attenuated, the viruses generated by the initial round of infection would be phenotypically attenuated. This approach can be applied to any virus that, upon the introduction of select mutations, can be propagated with an organism or system that utilizes an alternative genetic code.

28 Claims, 3 Drawing Sheets

PHENOTYPICALLY WILD-TYPE AND GENETICALLY ATTENUATED VIRUSES

CROSS-REFERENCE TO RELATED APPLICATIONS

This application is a U.S. National Stage Application filed under 35 U.S.C. § 371 of International Application No. PCT/US2018/035587, filed Jun. 1, 2018, which claims the benefit of U.S. Provisional Application No. 62/514,091, filed Jun. 2, 2017. Both of these applications are hereby incorporated by reference in their entireties.

FIELD OF THE INVENTION

The present invention relates to compositions and methods of producing live attenuated viruses.

BACKGROUND OF THE INVENTION

Live attenuated viral vaccines are some of the most effective vaccines currently used. Unlike inactivated or recombinant subunit vaccines, live attenuated viral vaccines infect the cells and replicate (to some extent), more closely mimicking a natural infection and, thus, inducing a more relevant immune response (e.g., presentation of intracellular foreign peptides on MHC class I molecules). Live attenuated vaccines include human measles, mumps, rubella, OPV, VZV, smallpox, yellow fever, and rotavirus vaccines, as well as several veterinary vaccines. To generate live attenuated vaccines, wild-type viruses have often been attenuated via passage in an unnatural host/tissue culture, in which they accumulate random mutations, some of which result in attenuation in the natural host but still allow for sufficient replication/propagation in cell culture. It is an inefficient empirical approach that relies on chance mutations.

Alternative, more rational approaches that have been attempted include introducing suboptimal codons for a given amino acid, reducing the efficiency of viral production; and cell line complementation, where, e.g., critical viral genes are removed from the virus and introduced into the production cell line, enabling the generation of structurally wild-type viral particles that encapsulate an incomplete genome. Such an approach generates a replication-incompetent vaccine where the viral vaccine can initially infect the vaccine's cells, but, as the vaccine's cells do not include the missing viral genes, they cannot generate live viruses and further propagate the infection.

Ideally, a live attenuated vaccine maintains the ability to infect cells and replicate/spread to a sufficient extent to induce a robust immune response, but without inducing disease. In sum, the challenge is generating a virus that replicates reliably and to a very high titer in the manufacturing cell lines, hence reducing production costs, yet is attenuated in the vaccine—i.e., is weakened to the point where it replicates in the vaccine and maintains most, if not all, of the relevant epitopes as the wild-type virus, to generate robust immunity, but is not virulent enough to cause disease.

SUMMARY OF THE INVENTION

The compositions and methods described herein provide viruses and vaccines based on viruses that have a wild-type amino acid sequence but are genetically attenuated. i.e. the genetically mutated viruses (vaccines) are phenotypically wild-type when propagated in a production cell culture or a cell-free system with a non-standard genetic code, which compensates for the genetic attenuation. Due to the genetic attenuation, the viruses become phenotypically attenuated only after one round of replication in a vaccine cell that translates proteins with the standard genetic code.

In one aspect, the genetically attenuated virus is generated by strategically introducing point mutations into the viral genome that result in codons that preserve the resulting amino acid sequence when translated with a cell line that employs an alternative (non-standard) genetic code, but result in residue substitutions when translated with the standard genetic code. (Henceforth, we'll refer to these unique codons, which are translated differently depending upon the code utilized, as 'amphicodons'.) The genetically attenuated virus is propagated in the alternative code cell line. The resultant phenotypically wild-type (still genetically attenuated) vaccine is purified and formulated for administration to a vaccine, in whom only phenotypically attenuated, yet still replication-competent, viruses are then generated.

In another aspect, when propagated in the alternative code cell line, the genetically attenuated virus that results will be phenotypically wild-type. However, while it will be phenotypically wild-type when translated with the alternative code, it will be phenotypically attenuated when translated with the standard code. When introduced into a host that utilizes the standard genetic code, the virus would infect the cells as the wild-type virus would; however, due to the genetic attenuation resulting in amphicodons, translated differently between the alternative code and the standard code, the virus generated after one round of replication would have consistent amino acid substitutions at pre-defined positions. Hence, it may be able to undergo several rounds of replication and cellular infection post-vaccination, generating a robust immune response, but it would be attenuated to the extent that it could not cause disease.

In another aspect, the method of making a live, attenuated virus comprises providing a genetically attenuated virus, wherein the virus has been genetically attenuated by modification with at least one genetic mutation wherein if the codon comprising the mutation is translated under a select alternate genetic code, the mutant codon would not result in an amino acid substitution relative to wild-type but if the codon comprising the mutation is translated under the standard genetic code, the mutant codon would result in an amino acid substitution; culturing the virus in a first cell or a cell-free system which translates proteins with an alternate genetic code wherein a phenotypically wild-type, genetically attenuated virus is propagated; and collecting the cultured virus and introducing the virus to a vaccine, whose cells are infected by the phenotypically wild-type and genetically attenuated virus, but then translate proteins based on the standard genetic code thereby resulting in a genotypically and phenotypically attenuated virus.

In another aspect, the method of making a viral protein comprises providing a genetically attenuated virus, wherein the virus has been genetically attenuated by modification with at least one genetic mutation wherein if the codon comprising the mutation is translated under a select alternate genetic code, the mutant codon would not result in an amino acid substitution relative to the wild-type virus but if the codon comprising the mutation is translated under the standard genetic code, the mutant codon would result in an amino acid substitution; culturing the virus in a first cell or a cell-free system which translates proteins with an alternate genetic code wherein a phenotypically wild-type, genetically attenuated virus is propagated; and collecting the cultured virus and introducing the virus to a vaccine, whose cells are infected by the phenotypically wild-type and genetically attenuated virus, but which translates proteins based on the standard genetic code thereby resulting in a viral protein, wherein the protein is unable to generate/form viable viral progeny, but is capable of eliciting a response from a host immune system.

In connection with the various aspects of the disclosed compositions and methods, in some embodiments the alternate genetic code is Code 12; at least one genetic mutation is a substitution of a codon selected from the group consisting of UCU, UCC, UCA, UCG, AGU, and AGC and combinations thereof with the codon CUG; the first cell (alternate genetic code cell) is a cell of a species within the genus *Candida* that utilizes Code 12; the alternate genetic code is Code 26; at least one genetic mutation is a substitution of a codon selected from the group consisting of GCU, GCC, GCA, and GCG and combinations thereof with the codon CUG; the first cell (alternate genetic code cell) is a cell of species in the genus *Pachysolen* that utilizes Code 26; the alternate genetic code is one of the several codes which codes for an amino acid with a codon that codes for a termination codon in the standard code; and/or the virus is selected from the group consisting of Influenza virus, respiratory syncytial virus (RSV), poliovirus, Hepatitis C virus, West Nile virus, Zika virus, Chikungunya virus, Ebola virus, Lassa virus, Dengue virus, SARS coronavirus, Middle East Respiratory Syndrome (MERS) coronavirus, Cytomegalovirus, Herpes Simplex viruses, Rabies virus, Foot and Mouth Disease Virus, Noroviruses, Enteroviruses, newly emerging viruses, as well as combinations thereof.

In another aspect, a live, attenuated virus and/or viral protein made by the methods described herein is disclosed.

In another aspect, a method of vaccinating a subject is disclosed, comprising inoculating the subject with a live, attenuated virus and or viral protein as disclosed herein.

In another aspect, the subject of the vaccination is a human, livestock, a bird, a household pet, wildlife, or a plant.

In another aspect, an article of manufacture is disclosed comprising a live, attenuated virus and/or viral protein as described herein.

DETAILED DESCRIPTION

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

All documents, or portions of documents, cited in this application, including but not limited to patents, patent applications, articles, books, and treatises, are hereby expressly incorporated by reference in their entirety.

As used herein, "a" or "an" may mean one or more than one of an item.

As used herein, "about" may mean up to and including plus or minus five percent, for example, about 100 may mean 95 and up to 105.

As used herein, and for simplification of the language, "virus", and derivatives of this word (e.g., 'viral'), refers to both viruses and other infectious entities/agents with genetic material translated in host cells, with host tRNAs, during its lifecycle; or to infectious agents that can utilize exogenously supplied tRNAs in a cell-free system.

As used herein, "attenuated virus" means a virus that demonstrates reduced or no clinical signs of disease when administered to a eukaryote, including but not limited to an animal or plant. As used herein, "genetically attenuated" means having any mutation purposely introduced into the wild-type viral genome which could cause a phenotypically detrimental substitution of one or more amino acids in the protein or proteins translated based on the standard genetic code. As used herein "phenotypically attenuated" means having a phenotypically detrimental substitution of one or more amino acids in the protein or proteins that comprise it, such that a reduction in fitness of the virus results. As used herein, "attenuated virus" refers to a virus that is either solely genetically attenuated (and phenotypically wild-type) or both genetically and phenotypically attenuated.

As used herein, "alternate (genetic) code", "non-standard (genetic) code", "alternative (genetic) code", or "alternate nuclear code" means any code for translation of codons from nucleic acid into protein which is not the standard genetic code. For example, Code 12 is an alternate genetic code utilized by the yeast species *Candida albicans, Candida cylindracea, Candida melibiosica, Candida parapsilosis, Candida rugosa*, and potentially other uncharacterized organisms.

As used herein, "propagate" means reproduction, including but not limited to reproduction for manufacture of an attenuated virus for use in a vaccine.

As used herein, "vaccine" means a vaccinated subject.

Herein, examples are given which utilize the nucleotide uracil (U), used by RNA viruses. However, in the case of DNA viruses (covered by this disclosure as well), one of ordinary skill in the art would understand to substitute uracil (U) for thymine (T) to apply the disclosed methods.

Note that, when illustrating the embodiments described in this application, positive sense RNA viral genomes are described for simplicity. However, in all instances, this can be understood to be the mRNA of a negative sense RNA virus, a double stranded RNA virus, and/or a DNA virus and the described mutations would be at the corresponding locations in the genome.

The compositions and methods described herein provide viruses and vaccines based on viruses that have a wild-type amino acid sequence (i.e., proteins with wild type sequences) but are genetically attenuated, i.e. are phenotypically wild-type, when propagated in a production cell culture or a cell-free system with a non-standard genetic code which compensates for the genetic attenuation. Due to the genetic attenuation, the viruses become phenotypically attenuated after one round of replication in a cell which translates mRNA to protein using the standard genetic code.

Figure 1:
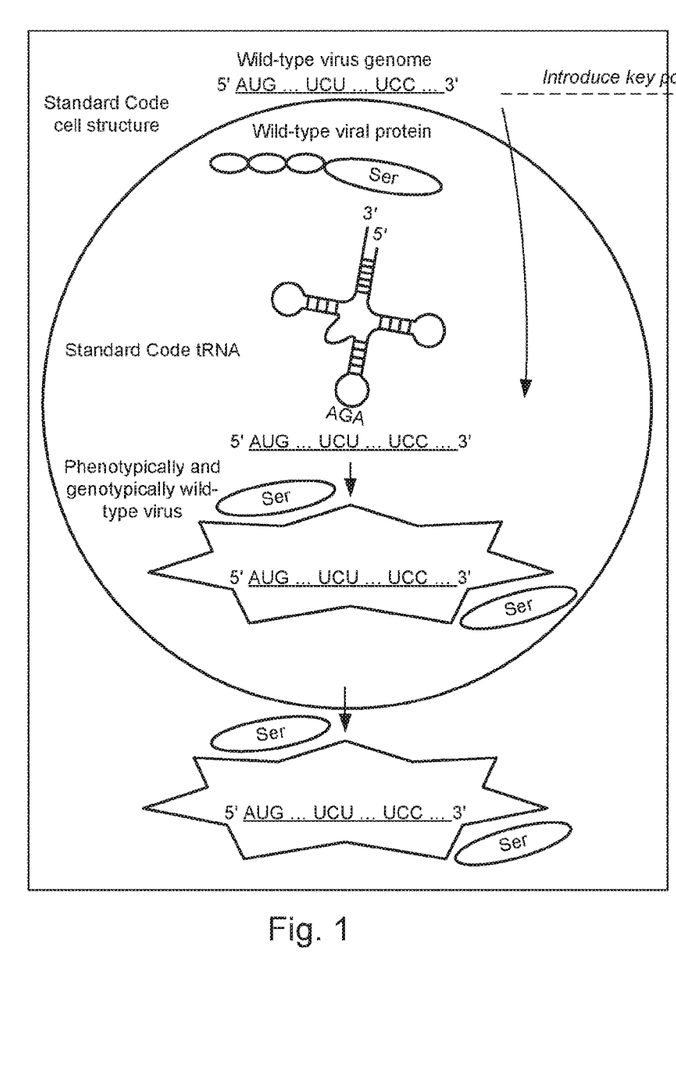
FIG. 1 illustrates an example of a wild-type virus propagated in a standard-code cell culture. The propagated virus is both phenotypically and genotypically wild-type.
Figure 2A:
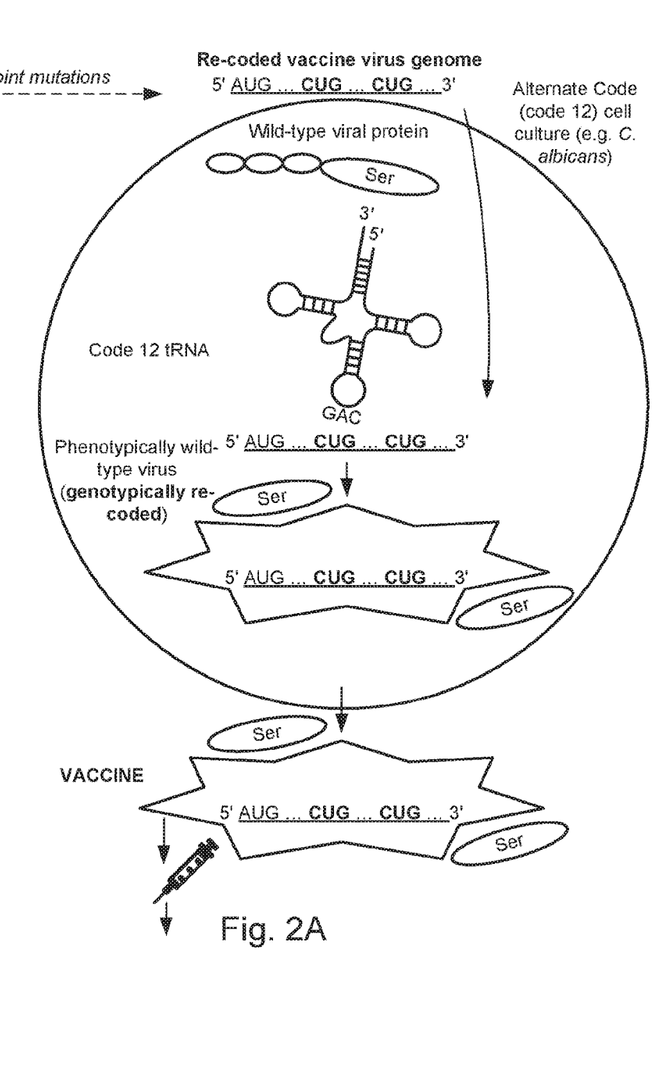
FIG. 2A illustrates an example of a genetically attenuated virus propagated in an alternate-code cell culture. The propagated virus is phenotypically wild-type but remains genotypically attenuated.
Figure 2B:
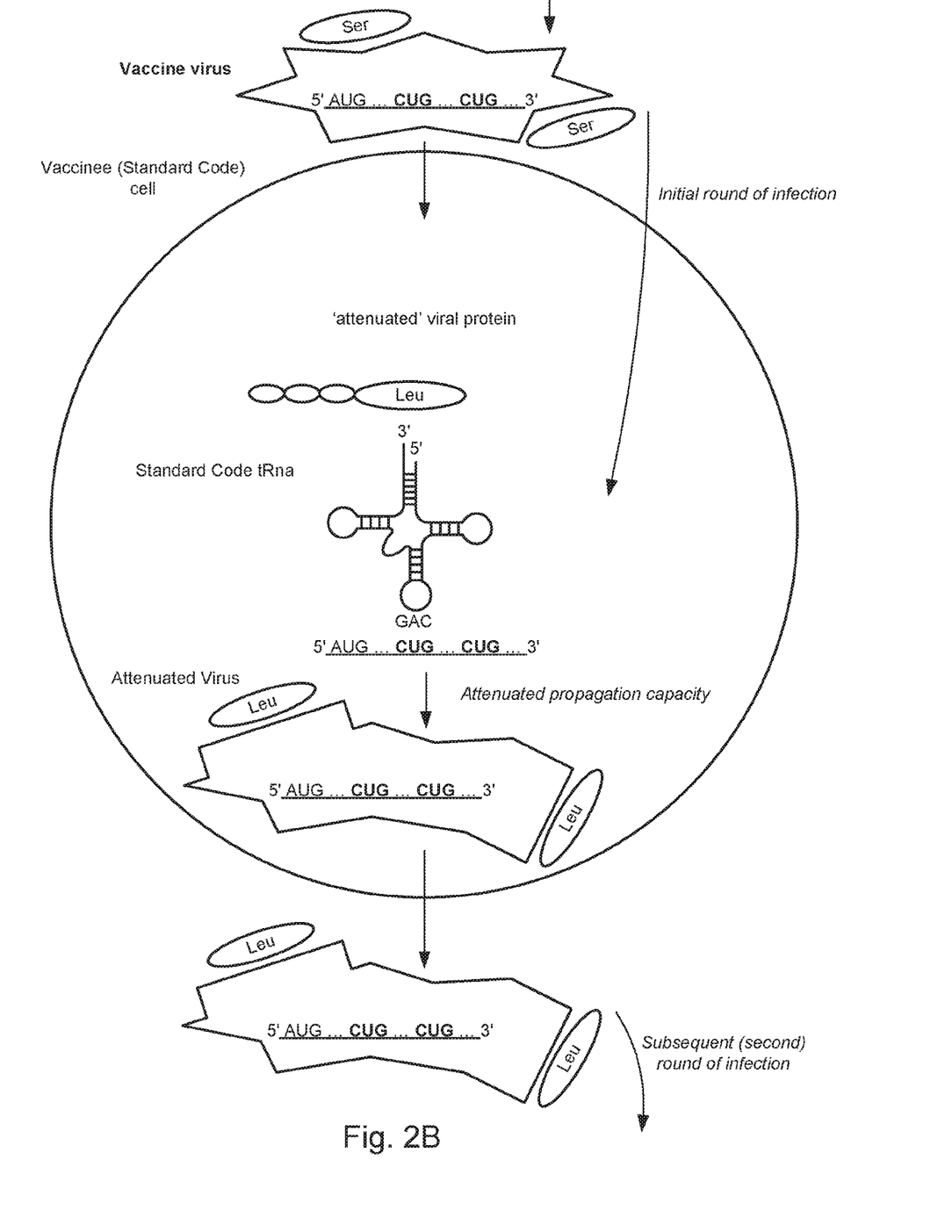
FIG. 2B illustrates the genetically attenuated virus generated in 2A, having entered a standard-code cell (e.g., the vaccine cell) as a phenotypically wild-type virus, propagated in the context of this standard-code. The propagated virus is both phenotypically and genotypically attenuated.
Figure 2C:
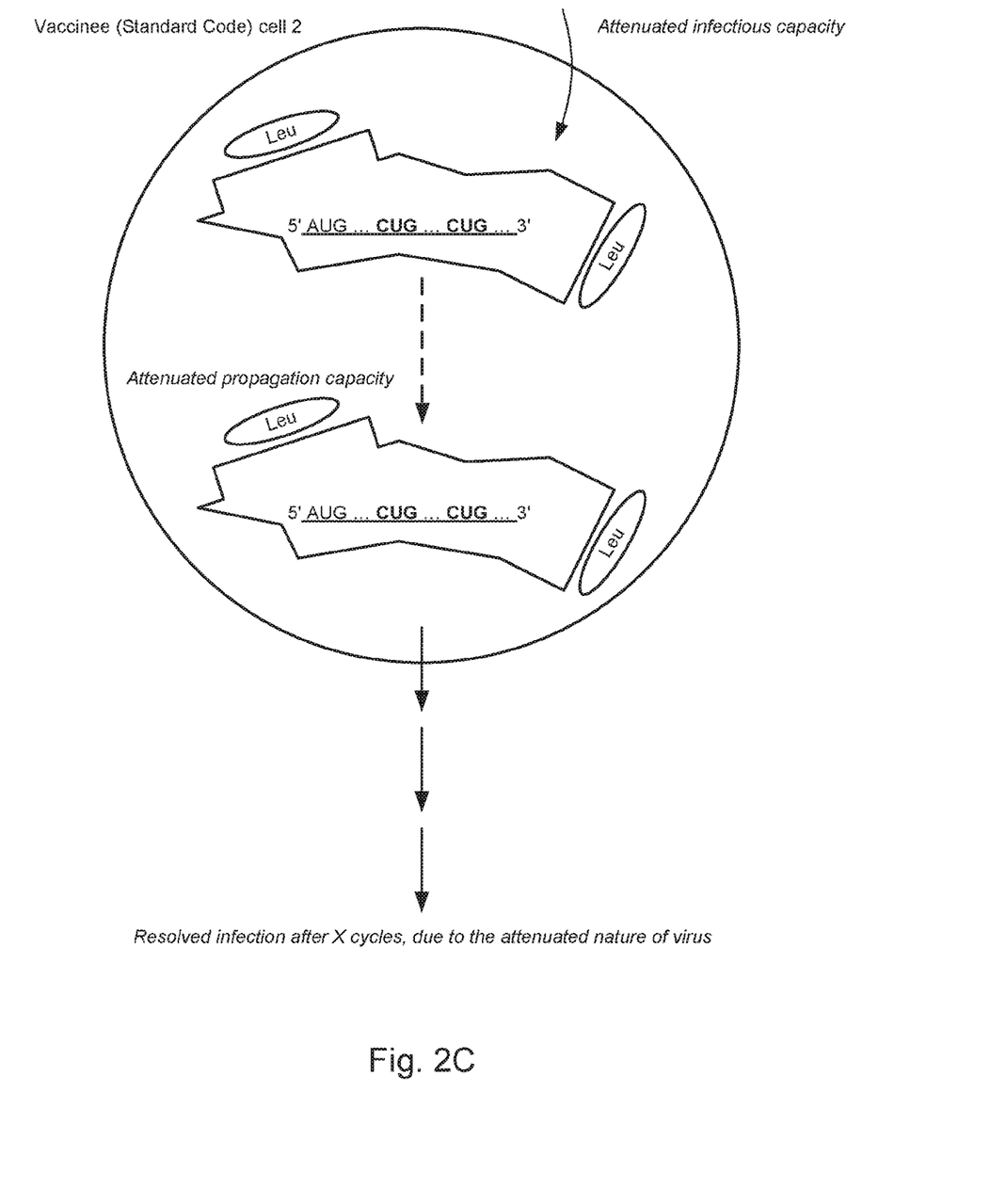
FIG. 2C illustrates the genetically/phenotypically attenuated virus from 2B further propagated in the standard-code host (vaccine). The virus continues to be both phenotypically and genotypically attenuated.

When propagated in the alternative code cell line (production cell culture or cell-free system), the virus will be phenotypically wild-type because the cognate tRNA of the amphicodon in the alternative code cell line compensates for the mutation in the codon, by carrying the wild-type amino acid for that position, and translates the wild-type amino acid in the coded protein or peptide sequence, see FIG. 2. However, while it will be phenotypically wild-type when translated with the alternative code, it will be phenotypically attenuated when translated with the standard code, see FIG. 2B. When introduced to a cell with the standard genetic code, the virus would infect the cell as the wild-type virus would; however, due to the genetic mutations resulting in codons translated differently between the alternative code and the standard code, the virus generated after one round of replication would have amino acid substitutions at pre-defined positions (the locations of the selected mutations; i.e., at the amino acids encoded by the amphicodons). Hence, the virus may be able to undergo several rounds of cellular infection, generating a robust immune response, but would be attenuated to the extent that it could not cause disease.

In one embodiment, point mutations are introduced in select locations of the genetic code of a selected virus. The point mutations are selected such that, in the non-standard code production culture, the codon comprising the point mutation(s) (the amphicodon) codes for the phenotypically wild-type amino acid despite the point mutation. Whereas, when the virus is replicated in a standard code cell, the selected mutations result in (i.e., the amphicodon codes for) an amino acid substitution, i.e. replacement with an amino acid which causes, at least in part, phenotypic attenuation of the virus. The number of mutations can be selected to provide a live, attenuated virus which is capable of propagation or can be selected to provide virus incapable of propagation or can be selected to provide a viral protein which is unable to generate viable viral progeny but which is capable of eliciting a response from a host immune system.

The vaccine may be produced by utilizing any cell line, organism or cell-free system that employs an alternative (non-standard) genetic code and by strategically introducing point mutations into the viral genome that preserve the amino acid sequence when translated with the alternative code cell line, but that result in residue substitutions when translated with the standard host code. Any organism that utilizes a genetic code different from the standard code, presents a potential cellular substrate (Jukes T H and Osawa S "Evolutionary changes in the genetic code" Comp Biochem Physiol B. 1993 November; 106(3):489-94; Osawa S et al. "Recent evidence for evolution of the genetic code". Microbiol Rev. 1992 March; 56(1):229-64).

Alternate genetic codes in mitochondria may also be used for the vaccine preparation. Trafficking signals on the nucleic acid are optionally employed to facilitate transport of the viral genome to the mitochondria.

It is recognized that many alternate codes have codons which code for an amino acid, whereas the same codons code for termination in the standard code. Hence, applying the strategy outlined in this invention (and altering the viral genome with strategic substitutions that result in wild type proteins in the alternative host) would result in proteins that prematurely terminate when replicated in standard code cells. Such alternate codes may under certain circumstances be employed for the composition and methods disclosed herein. See Example 3 below.

It is noted that if there are instances where an amphicodon (with different translations in the select propagation and vaccine code) appears in the wild-type virus and one wishes to maintain its standard translation (particularly relevant when one of the translations is termination) in the vaccine strain, it will be necessary to replace it with a non-amphicodon that has the desired translation (e.g., in the example directly above, if UGA is employed as a stop codon in the wild-type virus, one would want to change it to, e.g., UAA when introducing the strategic recoding of select UGU and UGC codons to UGA). Also note that if the alternative code selected for the propagation of the virus has additional non-standard initiation codons, the effect of this would need to be examined experimentally.

Preferred organisms for the compositions and methods of producing vaccines described herein include but are not limited to, the subset of organisms that use the alternative Code 12, including but not limited to *Candida albicans, Candida cylindracea, Candida melibiosica, Candida parapsilosis*, and *Candida rugose* as well as those that utilize the alternative code 26, including but not limited to *Pachysolen tannophilus* (See *Genome Res.* 2016 July; 26(7):945-55. doi: 10.1101/gr.200931.115. Epub 2016 May 6).

As additional species are identified in underexplored environments, it is highly likely that many of these species will utilize alternative codes, either similar to those already characterized, or novel. All such species may be used for the compositions and methods described herein, based on their variations from the standard genetic code.

Cell-free expression systems which provide for alternatives to the standard genetic code may also be used to propagate the vaccine virus. Such cell-free systems could obviate the need for a cellular substrate for propagation of the attenuated (vaccine) form of the target infectious entity. In an alternate genetic code cell-free system, cognate tRNAs for a mutant codon would be charged with the amino acid encoded by the wild-type virus at that position. In the vaccine, the mutated codon's standard code cognate tRNA would be used, resulting in a mutated peptide sequence. In vitro translation systems (particularly those capable of generating viruses with appropriate post-translational modifications) provide another embodiment of vaccine production comparable to the *Candida* cultures. One would generate an 'altered genetic code' of one's choice, with desired coding discrepancies (i.e., any codon could be an amphicodon), in an in vitro translation system.

The selection of mutations will be based on the level and type of phenotypic attenuation desired. Depending upon where in a particular virus one wishes to introduce alternative amino acids during replication in the vaccine (i.e., optimal substitutions for the desired level of attenuation), viruses may be mutated at any of many viral codons (throughout), depending upon the exact discrepancy (which is being exploited here) between the alternative code and the standard code. Mutations can be made to a single codon in a virus, more than one instance of the codon in a virus, or all instances of the codon in the virus. Further, mutations can be made to one or more than one type of codon (each type being a combination of three nucleotides coding for a different amino acid and/or peptide termination), and one or more than one instance of each type of codon in the viral genome.

The compositions and methods of producing vaccines described herein may be performed, if multiple types of codons are substituted, in an alternate genetic code system in which the cognate tRNAs for each type of mutant codon are charged with the amino acid encoded by the codon pre-mutation (as it would be in the standard code pre-mutation), followed by propagation of the virus in an alternate code system, whether with a cell substrate or cell-free.

Note that, when illustrating the embodiments described in this application, positive sense RNA viral genomes are described for simplicity. However, in all instances, this can be understood to be the mRNA of a negative sense RNA virus, a double stranded RNA virus, and/or a DNA virus and the described mutations would be at the corresponding locations in the genome.

Embodiments include compositions and methods for live attenuated viruses including, but not limited to, Picornaviruses (e.g., hepatitis A virus, enteroviruses such as poliovirus, enterovirus 71, 70, 69, and 68, Coxsackieviruses, echoviruses, foot and mouth disease virus, and rhinoviruses), Caliciviruses (e.g., hepatitis E virus, noroviruses such as Norwalk virus, feline calicivirus), Arteriviruses (e.g., equine arteritis virus), Togaviruses (e.g., sindbis virus, the equine encephalitis viruses, chikungunya virus, rubella virus, Ross River virus, bovine diarrhea virus, hog cholera virus, Semliki forest virus), Flaviviruses (e.g., dengue virus, West Nile virus, yellow fever virus, Japanese encephalitis virus, St. Louis encephalitis virus, tick-borne encephalitis virus, bovine viral diarrhea virus, classical swine fever virus), Coronaviruses (e.g., human coronaviruses, including SARS and MERS, swine gastroenteritis virus), Rhabdoviruses (e.g., rabies virus, Australian bat lyssavirus, vesicular stomatitis viruses), Filoviruses (e.g., Marburg virus, Ebola virus), Paramyxoviruses (e.g., measles virus, canine distemper virus, mumps virus, parainfluenza viruses, respiratory syncytial virus, Newcastle disease virus, rinderpest virus, Nipah virus, Hendra virus), Orthomyxoviruses (e.g., human influenza viruses, avian influenza viruses, equine influenza viruses), Bunyaviruses (e.g., hantavirus, LaCrosse virus, Rift Valley fever virus), Arenaviruses (e.g., Lassa virus, Machupo virus), Reoviruses (e.g., human and animal reoviruses, such as rotaviruses, bluetongue virus), Birnaviruses (e.g., infectious bursal virus, fish pancreatic necrosis virus), Retroviruses (e.g., HIV 1, HIV 2, HTLV-1, HTLV-2, bovine leukemia virus, feline immunodeficiency virus, feline sarcoma virus, mouse mammary tumor virus), Hepadnaviruses (e.g., hepatitis B virus), Parvoviruses (e.g., B19 virus, canine parvovirus, feline panleukopenia virus), Papovaviruses (e.g., human papillomaviruses, SV40, bovine papillomaviruses), Adenoviruses (e.g., human, canine, bovine, and porcine adenoviruses), Herpesviruses (e.g., herpes simplex viruses, varicella-zoster virus, infectious bovine rhinotracheitis virus, cytomegalovirus, human herpesvirus 6, human herpesvirus 7, human herpesvirus 8, Epstein-Barr virus), Poxviruses (e.g., vaccinia, fowlpoxviruses, raccoon poxvirus, skunkpox virus, monkeypoxvirus, cowpox virus, buffalopox virus, musculum contagiosum virus). Newly identified and emerging families, types, species, and strains of viruses may also be used in the compositions and methods described herein. Any virus that, when select mutations are introduced, can be propagated in an alternative genetic code system, may be used.

Some embodiments herein relate to compositions for live, attenuated viruses in any final form, e.g., aqueous or lyophilized/freeze-dried form. Those skilled in the art will recognize that formulations that improve thermal viral stability and prevent freeze-thaw inactivation will improve products that are liquid, powdered, freeze-dried or lyophilized and prepared by methods known in the art. After reconstitution, such stabilized vaccines can be administered by a variety of routes, including, but not limited to intradermal administration, subcutaneous administration, intramuscular administration, intranasal administration, pulmonary administration or oral administration. A variety of devices are known in the art for delivery of the vaccine including, but not limited to, syringe and needle injection, bifurcated needle administration, administration by patches or pumps, needle-free jet delivery, intradermal particle delivery, or aerosol powder delivery.

Embodiments can include compositions consisting of one or more live attenuated viruses (as described above) and a mixture of one or more excipients (e.g., high molecular weight surfactants and one or more proteins in a physiologically acceptable buffer). In certain embodiments, compositions may or may not include, but are not limited to one or more live attenuated viruses, one or more high molecular weight surfactants, one or more proteins, and one or more carbohydrates, in a physiologically acceptable buffer.

An additional application of the approach described here would be for a safer inactivated vaccine via a seed strain genotypically attenuated in the natural host. For example, such an approach would be particularly well-suited for an inactivated viral vaccine (e.g., IPV) against a pathogen that is being eradicated (e.g. poliovirus), where wild-type viruses (including seed viruses in vaccine manufacturing) need to be eliminated globally and live attenuated viral vaccines (OPV) are no longer acceptable for administration to vaccines. Such an approach would result in a safer inactivated viral vaccine (e.g., 'safer IPV'), where the seed virus has a wild-type phenotype but a genotype that would be attenuated in the natural host population, from which it is being eradicated. Hence, if the seed virus were released in a host population (whether by accident, intentionally, or as a result of incomplete inactivation during manufacturing), it would be severely compromised in its ability to spread.

In another aspect, if one does not desire a replication-competent virus generated after the initial round of infection in the vaccine, attenuation can be more extreme (by selecting the number and nature of codon substitutions), to the point where viral proteins are generated, but key ones are mutated enough so viable viral progeny cannot be generated. Namely, a wild-type like initial infection but no subsequent infection, only production of large amounts of viral proteins for presentation to the host immune system.

Pharmaceutical Compositions

Embodiments herein provide for administration of compositions to subjects in a biologically compatible form suitable for pharmaceutical administration in vivo. By "biologically compatible form suitable for administration in vivo" it is meant a form of the active agent (e.g. live, attenuated virus composition of the embodiments) to be administered in which any toxic or otherwise adverse effects are outweighed by the therapeutic or prophylactic effects of the active agent. Administration of a therapeutically or prophylactically active amount of the therapeutic or prophylactic composition is defined as an amount effective, at dosages and for periods of time necessary to achieve a desired result, including but not limited to increased immunity to a viral pathogen. For example, a therapeutically or prophylactically active amount of a compound may vary according to factors such as the disease state, age, sex, and weight of the individual, and the ability of formulations to elicit a desired response in the individual, including but not limited to a response which boosts immunity to a viral pathogen. Dosage regimen may be adjusted to provide the optimum therapeutic and/or prophylactic response.

In some embodiments, composition (e.g. pharmaceutical chemical, protein, peptide of an embodiment) may be administered in a convenient manner such as subcutaneous, intravenous, intramuscular, intradermal, by oral administration, inhalation, transdermal application, intravaginal application, topical application, intranasal or rectal administration. In a more particular embodiment, the product may be orally or subcutaneously administered. In another embodiment, the product may be administered intravenously. In one embodiment, the product may be administered intranasally, such as inhalation. In another embodiment, the product may be administered intramuscularly. In another embodiment, the product may be administered intradermally.

Kits

Further embodiments concern kits for use with methods and compositions described herein. Compositions and live virus formulations may be provided in the kit. The kits may also comprise bioinformatics tools (e.g., for the rapid assisted genetic design of the viral vaccines described herein), and/or can include a suitable container, live, attenuated virus compositions detailed herein and optionally one or more additional agents such as other anti-viral agents, anti-fungal, anti-bacterial and/or anti-parasite agents.

EXAMPLES

The following examples are provided for illustrative purposes only and are not intended to limit the scope of the invention as defined by the appended claims. All examples described herein were carried out using standard techniques, which are well known and routine to those of skill in the art.

Example 1

Code 12 is the nuclear code utilized by the yeast species *Candida albicans, Candida cylindracea, Candida melibiosica, Candida parapsilosis,* and *Candida rugosa* (Ohama, T et al. "Non-Universal Decoding of the Leucine Codon CUG in Several *Candida* Species." Nucleic Acids Research 21.17 (1993): 4039-4045. Print).

CUG, in the standard code, codes for Leucine (a neutral non-polar amino acid). CUG, in Code 12, codes for Serine (a neutral polar amino acid). As such, a subset of *Candida* species which utilize Code 12 are one embodiment of a substrate cell line that would support the above approach.

| | Resulting Amino Acid | |
|---|---|---|
| Codon | Standard Code | Code 12 (*Candida* Nuclear Code) |
| UCU | S | S |
| UCC | S | S |
| UCA | S | S |

| | Resulting Amino Acid | |
|---|---|---|
| Codon | Standard Code | Code 12 (*Candida* Nuclear Code) |
| UCG | S | S |
| AGU | S | S |
| AGC | S | S |
| CUG | L | S |
| CUA | L | L |
| CUC | L | L |
| CUU | L | L |
| UUG | L | L |
| UUA | L | L |

To rationally design a live attenuated virus (genotypically attenuated and phenotypically wild-type) with Code 12—utilizing *Candida* cells as the non-standard propagating (manufacturing) cell line (1) Begin with the virus's wild-type nucleotide code.

(2) At codons that code for Serine in the standard code (UCU, UCC, UCA, UCG, AGU, and AGC), one may replace the codon with CUG, which still codes for Serine in Code 12, but which will code for Leucine in the standard code. Replace any desired fraction of the viral standard-code Serine codons with CUG, depending upon the predicted essential/nonessential nature of the encoded residue and the degree of attenuation desired. Further, if the genome of the wild-type virus expresses CUG codons (which code for Leucine in the standard code), such codons would need to be mutated to a codon, such as CUU, which codes for Leucine in both standard and Code 12, so that codon would still code for Leucine when introduced into the alternative code cell.

(3) Introduce the altered viral genome into the *Candida* cells. Assuming the cells are both susceptible and permissive, the seed viruses generated are phenotypically wild-type yet genotypically attenuated in the context of an initial infection in a standard code host (e.g. human/animal) and genotypically wild-type in the context of the propagating *Candida* cells (Code 12).

(4) Propagate the virus in the *Candida* cells, purify, and formulate. The resulting vaccine should infect the vaccine's cells as a wild-type virus would, but the progeny will be attenuated.

Illustration—

(1) Wild-type virus typically codes as: AUG (M) AUA (I) ACA (T) *UCU (S)* AAA (K) AGA (R) *UCC (S)* . . . .
Wild-type virus is thus: M I T S K R S . . . .

(2) Recode so genetic code is: AUG AUA ACA *CUG* AAA AGA *CUG* . . . .
In Code 12 yeast, it is still: M I T *S* K R *S* . . . .
But when translated in a standard code host (e.g. human/animal) cell, it is: M I T *L* K R *L* . . . .

Replication of viruses in the cells of yeast, which are eukaryotes, provides for more mammalian-like post-translational modifications than if propagated in prokaryotes, making alternate code yeast a preferred candidate for a vaccine production system over prokaryotic cells. Yet, other eukaryotic and non-eukaryotic production cultures that use an alternative genetic code (or in vitro translation systems) are also expected to function in a manner similar to the *Candida* cultures.

Example 2

Code 26 Table (another potential example of a Code that can be exploited in a manner similar to Code 12, above):

| | Resulting Amino Acid | |
|---|---|---|
| Codon | Standard Code | Code 26 (*Pachysolen tannophilus* Nuclear Code) |
| GCU | A | A |
| GCC | A | A |
| GCA | A | A |
| GCG | A | A |
| CUG | L | A |
| CUA | L | L |
| CUC | L | L |
| CUU | L | L |
| UUG | L | L |
| UUA | L | L |

Example 3 Example 2

Illustrative Example—Where Termination Codon of Standard Code Codes for

Amino Acid

| | Resulting Amino Acid | |
|---|---|---|
| Codon | Standard Code | Euplotid Nuclear Code |
| UGU | C | C |
| UGC | C | C |
| UGA | Stop | C |
| UAG | Stop | Stop |
| UAA | Stop | Stop |

(1) Wild-type virus typically codes as: AUG (M) . . . AUA (I) *UGU (C)* . . . AGA (R) UAG (stop)
Wild-type virus is thus: M I *C* . . . R (stop)
(2) Recode so genetic code is: AUG . . . AUA *UGA* . . . AGA UAG . . . .
In Euplotid cells, it is still: M . . . I *C* . . . R (stop)
But when translated in a human/animal cell (the vaccine), it is: M . . . I (stop)

What is claimed is:

1. A method of making a live, attenuated virus comprising:
providing a genetically attenuated virus, wherein the virus has been genetically attenuated by modification with at least one genetic mutation wherein if the codon comprising the mutation is translated under a select alternate genetic code, the mutant codon would not result in an amino acid substitution relative to the wild-type virus but if the codon comprising the mutation is translated under the standard genetic code, the mutant codon would result in an amino acid substitution;
culturing the virus in a first cell or a cell-free system which translates proteins with an alternate genetic code wherein a phenotypically wild-type, genetically attenuated virus is propagated; and
collecting the cultured virus and introducing the virus to a vaccine, whose cells are infected by the phenotypically wild-type and genetically attenuated virus, but then translate proteins based on the standard genetic code thereby resulting in a genotypically and phenotypically attenuated virus.

2. The method of claim 1, wherein the alternate genetic code is Code 12.

3. The method of claim 1, wherein the at least one genetic mutation is a substitution of a codon selected from the group consisting of UCU, UCC, UCA, UCG, AGU, and AGC and combinations thereof with the codon CUG.

4. The method of claim 1, wherein the first cell is a cell of a species in the genus *Candida* that utilizes Code 12.

5. The method of claim 1, wherein the alternate genetic code is Code 26.

6. The method of claim 1, wherein at least one genetic mutation is a substitution of a codon selected from the group consisting of GCU, GCC, GCA, and GCG and combinations thereof with the codon CUG.

7. The method of claim 1, wherein the first cell is a cell of species in the genus *Pachysolen* that utilizes Code 26.

8. The method of claim 1, wherein the alternate genetic code is one which codes for an amino acid with a codon that codes for a termination codon in the standard code.

9. The method of claim 1, wherein the virus is selected from the group consisting of Influenza virus, respiratory syncytial virus (RSV), poliovirus, Hepatitis C virus, West Nile virus, Zika virus, Chikungunya virus, Ebola virus, Lassa virus, Dengue virus, SARS coronavirus, Middle East Respiratory Syndrome (MERS) coronavirus, Cytomegalovirus, Herpes Simplex viruses, Rabies virus, Foot and Mouth Disease Virus, Noroviruses, Enteroviruses, newly emerging viruses, as well as combinations thereof.

10. A live, attenuated virus made by the method of claim 1.

11. A method of vaccinating a subject, comprising inoculating the subject with the live, attenuated virus of claim 10.

12. The method of claim 11, wherein the subject is a human, livestock, a bird, a household pet, wildlife, or a plant.

13. An article of design and/or manufacture comprising the live, attenuated virus of claim 1.

14. A method of making a viral protein comprising:
providing a genetically attenuated virus, wherein the virus has been genetically attenuated by modification with at least one genetic mutation wherein if the codon comprising the mutation is translated under a select alternate genetic code, the mutant codon would not result in an amino acid substitution relative to the wild-type virus but if the codon comprising the mutation is translated under the standard genetic code, the mutant codon would result in an amino acid substitution;
culturing the virus in a first cell or a cell-free system which translates proteins with an alternate genetic code wherein a phenotypically wild-type, genetically attenuated virus is propagated; and collecting the cultured virus and introducing the virus to a vaccine whose cells are infected by the phenotypically wild-type and genetically attenuated virus, but which translates proteins based on the standard genetic code thereby resulting in a viral protein, wherein the protein is unable to generate viable viral progeny, but is capable of eliciting a response from a host immune system.

15. The method of claim 14, wherein the alternate genetic code is Code 12.

16. The method of claim 14, wherein the at least one genetic mutation is a substitution of a codon selected from the group consisting of UCU, UCC, UCA, UCG, AGU, and AGC and combinations thereof with the codon CUG.

17. The method of claim 14, wherein the first cell is a cell of a species in the genus *Candida* that utilizes Code 12.

18. The method of claim 14, wherein the alternate genetic code is Code 26.

19. The method of claim 14, wherein at least one genetic mutation is a substitution of a codon selected from the group consisting of GCU, GCC, GCA, and GCG and combinations thereof with the codon CUG.

20. The method of claim 14, wherein the first cell is a cell of species in the genus *Pachysolen* that utilizes Code 26.

21. The method of claim 14, wherein the alternate genetic code is one which codes for an amino acid with a codon that codes for a termination codon in the standard code.

22. The method of claim 14, wherein the virus is selected from the group consisting of Influenza virus, respiratory syncytial virus (RSV), poliovirus, Hepatitis C virus, West Nile virus, Zika virus, Chikungunya virus, Ebola virus, Lassa virus, Dengue virus, SARS coronavirus, Middle East Respiratory Syndrome (MERS) coronavirus, Cytomegalovirus, Herpes Simplex viruses, Rabies virus, Foot and Mouth Disease Virus, Noroviruses, Enteroviruses, newly emerging viruses, as well as combinations thereof.

23. A viral protein made by the method of claim 14.

24. A method of vaccinating a subject, comprising inoculating the subject with the viral protein of claim 14.

25. The method of claim 24, wherein the subject is a human, livestock, a bird, a household pet, wildlife, or a plant.

26. An article of design and/or manufacture comprising the live, viral protein of claim 14.

27. The method of claim 1, wherein the mutation is a substitution or a point mutation.

28. The method of claim 14, wherein the mutation is a substitution or a point mutation.

* * * * *